US010893967B2

(12) United States Patent
Ramos et al.

(10) Patent No.: US 10,893,967 B2
(45) Date of Patent: Jan. 19, 2021

(54) TECHNOLOGICAL CONGENITAL TALIPES EQUINO VARUS (CTEV) TREATMENT SUCCESS RATE IMPROVEMENT

(71) Applicant: International Business Machines Corporation, Armonk, NY (US)

(72) Inventors: Igor S. Ramos, Georgetown, TX (US); Ana C. Biazetti, Cary, NC (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 268 days.

(21) Appl. No.: 16/103,301

(22) Filed: Aug. 14, 2018

(65) Prior Publication Data

US 2020/0054474 A1 Feb. 20, 2020

(51) Int. Cl.
*A61F 5/01* (2006.01)
*G16H 20/30* (2018.01)
*A63F 13/65* (2014.01)
*A63F 13/212* (2014.01)
(Continued)

(52) U.S. Cl.
CPC .......... *A61F 5/0111* (2013.01); *A63F 13/212* (2014.09); *A63F 13/24* (2014.09); *A63F 13/65* (2014.09); *A63H 30/04* (2013.01); *G16H 20/30* (2018.01); *A63F 2300/1043* (2013.01);
(Continued)

(58) Field of Classification Search
CPC .... A61F 5/0111; A61F 5/0113; A61F 5/0195; A61F 5/14; G16H 20/30; G16H 40/67; A63F 13/212; A63F 13/218; A63F 13/24–245; A63F 13/90; A63F 2250/025; A63F 2300/1012; A63F 2300/105; A63F 2300/1062; A63F 2300/1043; A63F 2300/8094
See application file for complete search history.

(56) References Cited

U.S. PATENT DOCUMENTS 6,162,189 A 12/2000 Girone et al.
6,436,058 B1 8/2002 Krahner et al.
(Continued)

OTHER PUBLICATIONS

Shastri et al., Design of capacitative sensors for compliance monitoring in padmapada clubfoot brace, 3rd ISSE National Conference on Complex Engineering Systems of National Importance: Current Trends & Future Perspective (INAC-03), Oct. 2017. (Year: 2017).*
(Continued)

*Primary Examiner* — Thaddeus B Cox
(74) *Attorney, Agent, or Firm* — Fabian VanCott; Steven L. Nichols (57) ABSTRACT

Real-time cast sensor measurement outputs of a set of cast sensors that each measure a characteristic related to usage of an adjustable removable cast worn by a patient during treatment of congenital talipes equino varus (CTEV) are monitored. A cast usage anomaly relative to a treatment program prescribed for the patient with respect to wearing of the adjustable removable cast is identified according to the real-time cast sensor measurement outputs. Responsive to identifying the cast usage anomaly, real-time corrective treatment feedback is provided to the patient that instructs further and proper use of the adjustable removable cast to improve compliance with the treatment program prescribed for the patient.

20 Claims, 6 Drawing Sheets

(51) Int. Cl.
*A63F 13/24* (2014.01)
*A63H 30/04* (2006.01)

(52) U.S. Cl.
CPC ............... *A63F 2300/1062* (2013.01); *A63F 2300/8094* (2013.01)

(56) References Cited

U.S. PATENT DOCUMENTS

| | | | |
|---|---|---|---|
| 6,515,593 B1* | 2/2003 | Stark | A61B 5/411 |
| | | | 128/903 |
| 6,699,188 B2 | 3/2004 | Wessel | |
| 6,827,670 B1 | 12/2004 | Stark et al. | |
| 7,632,216 B2 | 12/2009 | Rahman et al. | |
| 9,230,057 B2 | 1/2016 | Stark et al. | |
| 2004/0030275 A1* | 2/2004 | Morinaka | A61F 5/0127 |
| | | | 602/27 |
| 2010/0324455 A1* | 12/2010 | Rangel | A43B 3/0005 |
| | | | 600/592 |
| 2013/0072838 A1* | 3/2013 | Fischer | A61F 13/04 |
| | | | 602/2 |
| 2013/0197414 A1* | 8/2013 | Northen | A61F 5/0116 |
| | | | 602/29 |
| 2016/0317084 A1 | 11/2016 | DeLuke et al. | |
| 2017/0091411 A1 | 3/2017 | Schoenecker et al. | |
| 2018/0311065 A1* | 11/2018 | Powell | A61F 5/0127 |
| 2018/0317847 A1* | 11/2018 | Ripperger, III | A61F 5/0195 |
| 2020/0030131 A1* | 1/2020 | Hanft | A61F 5/0111 |

OTHER PUBLICATIONS

Author Unknown, Boosting patient empowerment and motivational pull, Achieving the next level in a gamified health environment, Monitor Deloitte, Feb. 2016, pp. 1-32, Deloitte Touche Tohmatsu Limited, Published at: https://www2.deloitte.com/content/dam/Deloitte/de/Documents/strategy/Gamification%20Studie%202015.pdf.

Author Unknown, Clubfoot, Wikipedia, Aug. 8, 2018, pp. 1-9, Wikimedia Foundation, Inc., Published at: https://en.wikipedia.org/wiki/Club_foot.

S. Ahmad Al-Qerem, et al., Integrated monitoring application of patient progression: Clubfoot patient progression as case study, Abstract, In Proceedings of 2015 2nd World Symposium on Web Applications and Networking, Mar. 21, 2015, pp. 1-2, IEEE, Published at: http://ieeexplore.ieee.org/document/7210333/?reload=true.

P. K. Kammardi, et al., Compliance Monitored Clubfoot Brace "PADMAPADA," Conference Paper for ICoRD'15, Research into Design Across Boundaries, Dec. 24, 2014, pp. 559-568 (Abstract only, pp. 1-4), vol. 2, Springer, New Dehli, Published at: https://link.springer.com/chapter/10.1007/978-81-322-2229-3_47.

* cited by examiner

TECHNOLOGICAL CONGENITAL TALIPES EQUINO VARUS (CTEV) TREATMENT SUCCESS RATE IMPROVEMENT

BACKGROUND

The present invention relates to medical patient treatment. More particularly, the present invention relates to technological congenital talipes equino varus (CTEV) treatment success rate improvement.

Congenital talipes equino varus (CTEV) is a medical condition that is present at birth in approximately one in every one thousand (1,000) births. CTEV causes the newborn child's foot to be rotated inward and downward at the ankle, and is alternatively termed "clubfoot."

SUMMARY

A computer-implemented method of computer-controlled therapy includes monitoring real-time cast sensor measurement outputs of a plurality of cast sensors that each measure a characteristic related to usage of an adjustable removable cast worn by a patient during treatment of congenital talipes equino varus (CTEV); identifying, according to the real-time cast sensor measurement outputs, a cast usage anomaly relative to a treatment program prescribed for the patient with respect to wearing of the adjustable removable cast; and providing, responsive to identifying the cast usage anomaly, real-time corrective treatment feedback to the patient that instructs further and proper use of the adjustable removable cast to improve compliance with the treatment program prescribed for the patient.

A system that performs this optional computer-implemented method and a computer program product that causes a computer to perform the optional computer-implemented method are also described.

DETAILED DESCRIPTION

The examples set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

The subject matter described herein provides technological congenital talipes equino varus (CTEV) treatment success rate improvement. The present technology solves a recognized CTEV treatment problem by providing technology that includes a new form of integrated computing devices that improve real-time treatment feedback (e.g., corrective and/or recognition of treatment success), treatment compliance, and treatment adjustment across complex computing environments. The technology described herein provides distributed physicians, caregivers, and patients with an integrated treatment system in the form of a new Internet of things (IoT) medical treatment device and medical treatment system, and by use of the technology described herein provides a new technological treatment methodology to improve the success rate of treatment of CTEV. By monitoring the usage of the medical treatment device and providing real-time treatment feedback by use of IoT technologies, the system tracks the actual treatment activities performed by the patient against the prescribed usage, and from this evaluation provides real-time corrections to the actual treatment. By use of the real-time treatment feedback, the technology described herein further facilitates customized individualized treatment plans for individual patients/children according to how closely the particular patient is adhering to the prescribed treatment plan. A notification of the real-time treatment feedback may be provided as an electronic message sent to one of a smartphone, a tablet, and a game console designated to receive real-time corrective feedback notifications by one of a doctor, a parent, or a guardian of the patient to allow the doctor, the parent, or the guardian to assist the patient with social reinforcement of the patient's compliance with the treatment program. For purposes of the present description a doctor, a parent, or a guardian of the patient are each considered to be a "caregiver" herein, and the term caregiver may be utilized generally for brevity to refer to any such person that provides care to a patient. The technology described herein leverages gamification to encourage patients to use the medical treatment device the correct way for the correct period of time during each treatment period. By providing early and continual detection and correction of treatment non-compliance, the technology described herein can thereby reduce a need for surgeries that may otherwise result from treatment non-compliance. Additionally, by rapid detection that a particular patient is not responding to a treatment plan, alternative and/or additional treatments can be prescribed for the individual patient within the critical time period during which CTEV treatment can be successful without surgery. As an additional benefit, by integration of the real-time individualized treatment results across many patients, the actual CTEV treatment protocol itself can be adjusted and thereby improved.

Regarding monitoring by the IoT medical treatment device (hereinafter "IoT-MT device" for brevity), several physical aspects of a patient and the patient's treatment can be tracked using a variety of integrated real-time sensors. Each of these sensors may be selectively integrated with a patient's cast to achieve a variety of CTEV treatment improvements, and the cast is thereby considered to be a sensor-based cast throughout the present description. For example, an implementation of the IoT-MT device can include contact and/or pressure sensors and an integrated timer/clock to obtain wear time durations and wear time(s) of day during which the patient wears the IoT-MT device. Additionally, as appropriate for the given implementation and to increase confidence of caregivers that the IoT-MT device is being worn, the IoT-MT device can include a heartbeat sensor and a thermometer to sense patient heartbeat and temperature. The IoT-MT device can include a mechanical adjustable positioning system that records and sets wear angles relative to a previous foot angle or a target foot angle in certain implementations. A strain gauge that measures rotational tension around an axis of the foot can be integrated to record tension on the foot, again as appropriate for the given implementation. An accelerometer and a gyroscope can be integrated into the cast to measure and record activity and position data throughout the treatment.

Several technological features are available to integrate parental/caregiver supervision and engagement in the treatment. These are collectively termed "technological engagement approaches" for ease of reference herein. For example, in certain implementations, a caregiver can receive an alert, such as on a cell phone or other device, when the caregiver forgets to install the cast in preparation for the patient's sleep time. Additionally, in certain implementations, a graph can be shown with statistics regarding percentage of goal completion and other measures designed to encourage engagement by caregivers. Further, the caregiver can be engaged to be involved with the patient while the patient is wearing the cast as part of a game that is integrated into the caregiver's wrist watch or other device, as appropriate for the given implementation. As a further feature that assists with integration of caregiver engagement and supervision of a patient, and to provide support for the caregiver, additional relatives and caregivers can be added to the alerts and other technological engagement approaches to help expand the reach and reinforcement of monitoring of the progress of the treatment (e.g., an uncle, a godmother, a grandfather, etc.).

Several technological features are available to integrate patient/child engagement in the treatment. Given that the cast is technologically fitted with a variety of integrated sensors, as described above, the cast can be utilized to enable and control various forms of content in a television, a tablet computing device, and/or a phone or other mobile device, as appropriate for a given implementation. For example, in certain implementations, the patient can use the cast to control the user interface itself (e.g., to change channels on a television, etc.). Further, the patient can use the cast as a part of a game and/or game controller in video game implementations. One example implementation to further promote healing can include integrating the cast into a video game, with the cast simulated as a game object in the form of a surfboard, a skateboard, a roller skate, a bike shoe, or other game object for which a type of activity may be performed within the game that the patient may be currently unable to otherwise perform. In such an implementation, as the patient moves the cast, the cast controls a character in a game to turn the cast into a video game controller. In certain implementations, patients and caregivers can share the information about their journey/treatment with other patients and caregivers through the game to build a support network among similarly situated patients and caregivers. Cognitive technologies can be leveraged in certain implementations to build a history of stories, hints, tips, and techniques that can constantly be improved and shared with new patients and caregivers as they get started with CTEV treatment.

For doctors, the technology described herein can provide a tension study in certain implementations, such that a decrease in average tension indicates that the patient's foot has already moved the desired increment, and that it is time for further tension adjustment in the cast. In an opposite manner, a lack of decrease or an increase in average tension can indicate that the foot is not responding to the treatment and the doctor should evaluate whether the cast-based approach is still the proper treatment for the particular patient (i.e., whether surgical intervention is needed).

For researchers, the technology described herein can provide a relevant test hypothesis evaluation platform to test certain treatment hypotheses, such as a hypothesis that sleep position affects treatment effectiveness. Using the technology described herein, researchers can determine whether there is a treatment outcome correlation with respect to whether the patient sleeps tummy up or tummy down. This data capture, amongst a large population of patients, can form the basis for study and CTEV treatment improvements. The results of such a study may suggest a change to the treatment approach with respect to patient positioning during sleep relative to different positioning when awake. Many other alternatives for treatment CTEV analysis and improvement may be derived from the technology described herein, and all such improvements are considered within the scope of the technology described herein.

The technology described herein operates by a processor that provides computer-implemented and computer-controlled therapy. Real-time cast sensor measurement outputs of a set of cast sensors that each measure a characteristic related to usage of an adjustable removable cast worn by a patient during treatment of congenital talipes equino varus (CTEV) are monitored. A cast usage anomaly relative to a treatment program prescribed for the patient with respect to wearing of the adjustable removable cast is identified according to the real-time cast sensor measurement outputs. Responsive to identifying the cast usage anomaly, real-time corrective treatment feedback is provided to the patient that instructs further and proper use of the adjustable removable cast to improve compliance with the treatment program prescribed for the patient.

It should be noted that conception of the present subject matter resulted from recognition of certain limitations associated with congenital talipes equino varus (CTEV) treatment. For example, it was observed that CTEV is treatable during early childhood, and that, if patients properly follow their treatment plans, many patients may recover completely allowing them to be capable of walking and participating in athletics just as well as individuals born without CTEV. However, it was also observed that the treatment must be diligently followed by the patient/child within a very critical time period after birth of a child that is born with CTEV. It was further determined that many parents and children lack an appreciation for the complexities and critical timing of treatment of CTEV, and that children lack an ability to self-monitor and follow their treatment programs. It was determined that if left untreated or if available treatment programs are not properly completed, a child may be left to suffer with CTEV for a lifetime. For example, people with CTEV often appear to walk on their ankles or on the sides of their feet, which prevents routine movement and participation in many physical activities. It was observed that a treatment termed the "Ponseti" method, if correctly completed, may be successful in treating CTEV in ninety-five percent (95%) or more of the cases in which the program is correctly completed. Unfortunately, it was determined that too many patients fail to properly complete the treatment program, either because of discomfort or lack of parental awareness of deviations from the treatment plan, and that this failure to properly complete the treatment program results in certain children growing beyond the critical time period during which CTEV may be treated. For example, under the Ponseti method, a child must wear special shoes or braces full-time for three months, then just nightly for three years. However, to a young child, this duration of treatment appears to literally be a lifetime, and it is very difficult over such an extended period of time for a child to achieve full treatment success, either because the brace is uncomfortable or the duration of treatment is too burdensome. As a further consequence, it was determined that many people born with CTEV that could have been fully treated and cured fail to properly complete the treatment, and as a result unnecessarily enter later childhood and adulthood with CTEV that could have been cured. It was observed that there is no conventional solution by which CTEV treatment may be ensured to be properly completed. The present subject matter solves these problems with conventional treatment of CTEV by providing a technology-based solution that engages and supports patients, family, friends, and doctors to improve the CTEV treatment success rate during this critical period of time during which CTEV may be successfully treated. The technology described herein integrates the patient and patient's treatment activities with family, friends, and doctor(s) with real-time treatment feedback and adaptation of the treatment itself, as described above and in more detail below. As such, improved treatment success for CTEV may be obtained through use of the present technology.

The technological congenital talipes equino varus (CTEV) treatment success rate improvement described herein may be performed in real time to allow prompt feedback and adjustment of CTEV treatment to increase the rate at which treatment of CTEV is properly performed. For purposes of the present description, real time shall include any time frame of sufficiently short duration as to provide reasonable response time for information processing acceptable to a user of the subject matter described. Additionally, the term "real time" shall include what is commonly termed "near real time"—generally meaning any time frame of sufficiently short duration as to provide reasonable response time for on-demand information processing acceptable to a user of the subject matter described (e.g., within a portion of a second or within a few seconds). These terms, while difficult to precisely define are well understood by those skilled in the art.

Additional details of the algorithmic processing and computational efficiencies will be provided further below. The following portion of the present description provides examples of advanced computational platform(s) within which the present technology may be implemented, followed by further details of the technological congenital talipes equino varus (CTEV) treatment success rate improvement described herein.

It should be noted that the present technology may be implemented within or as part of a cloud computing environment (e.g., for data analytics), or may be implemented as a customized environment-specific solution. As such, examples of implementations for both environments are included herein.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 1:
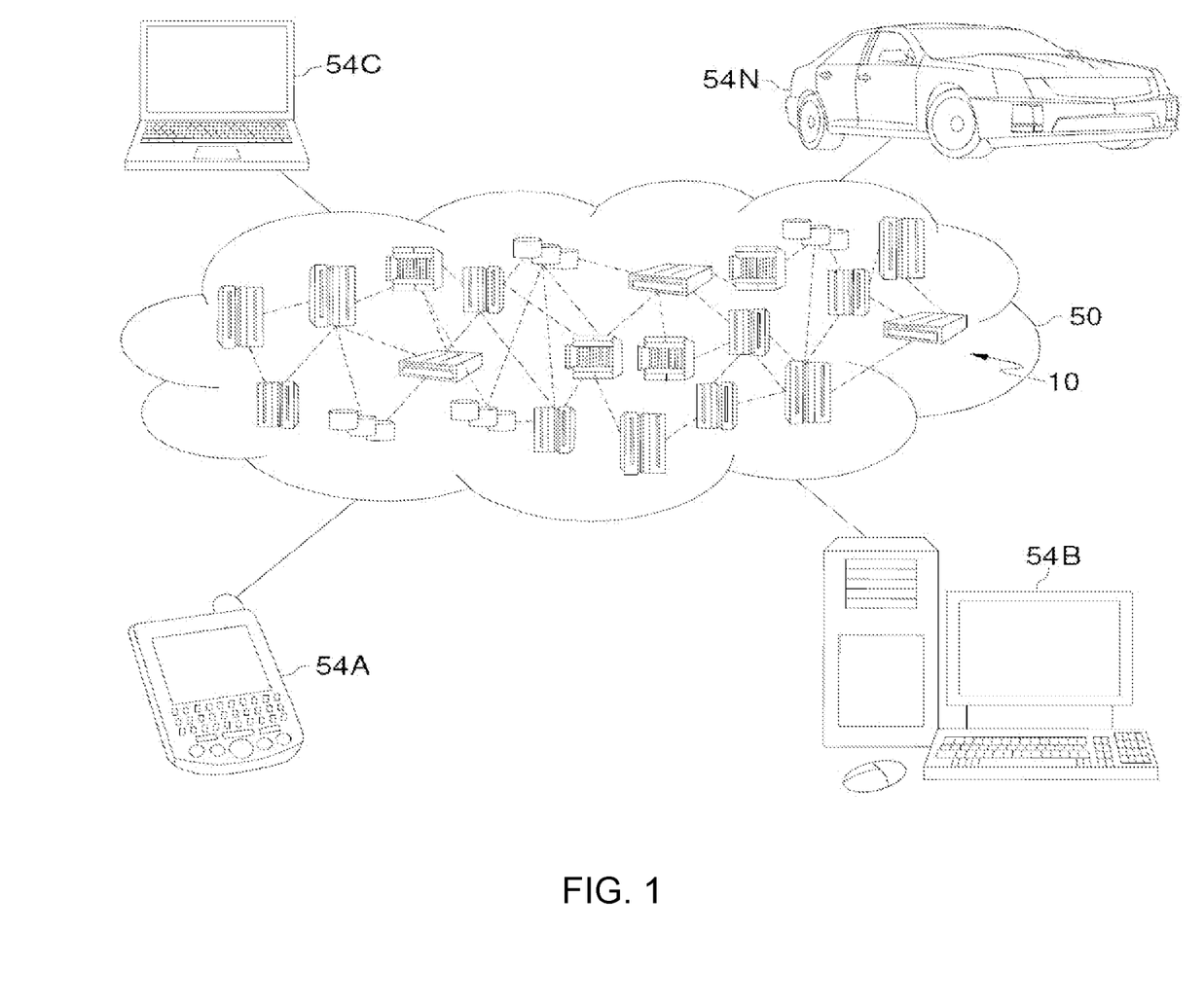
FIG. 1 depicts a cloud computing environment according to an embodiment of the present invention.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
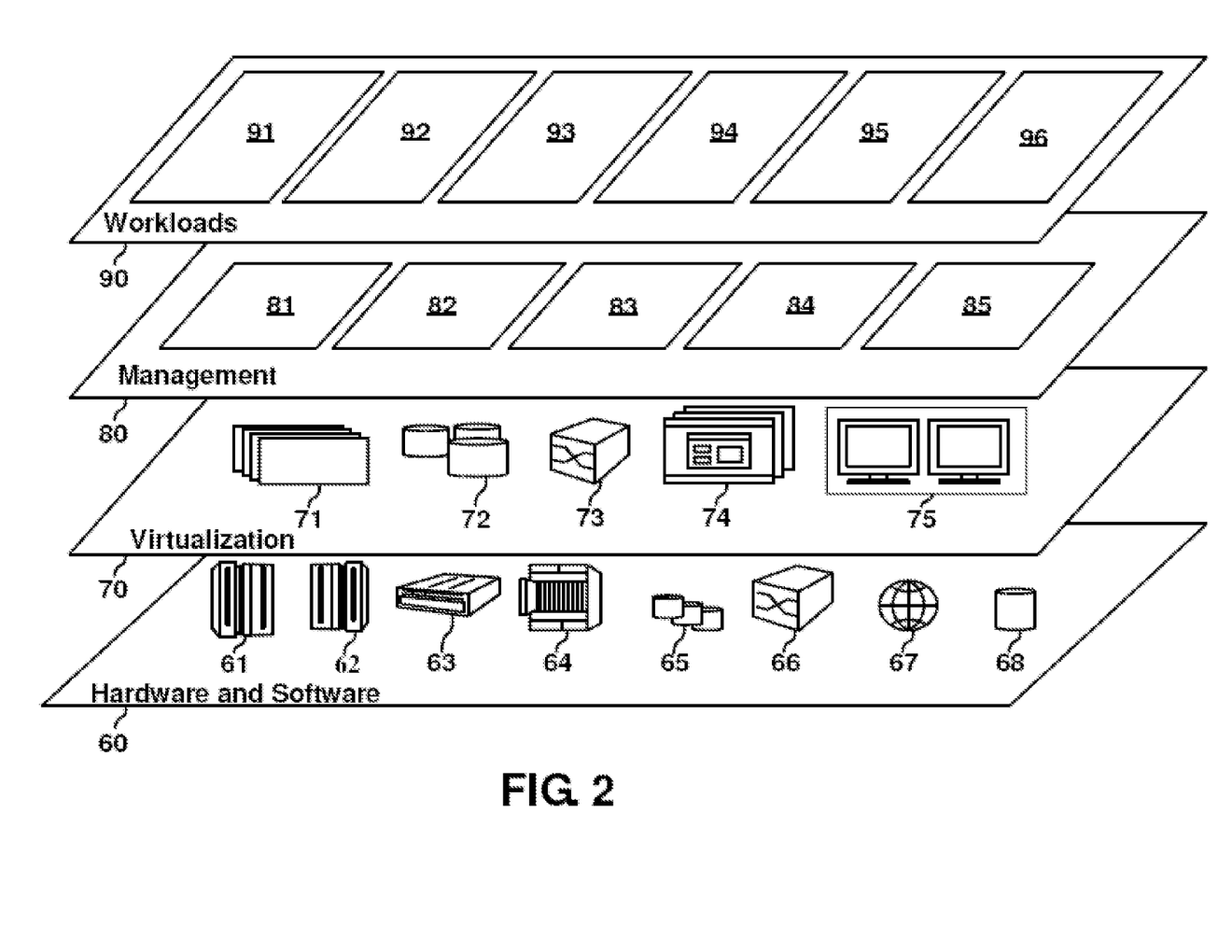
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and technological CTEV treatment success rate improvement 96.

Figure 3:
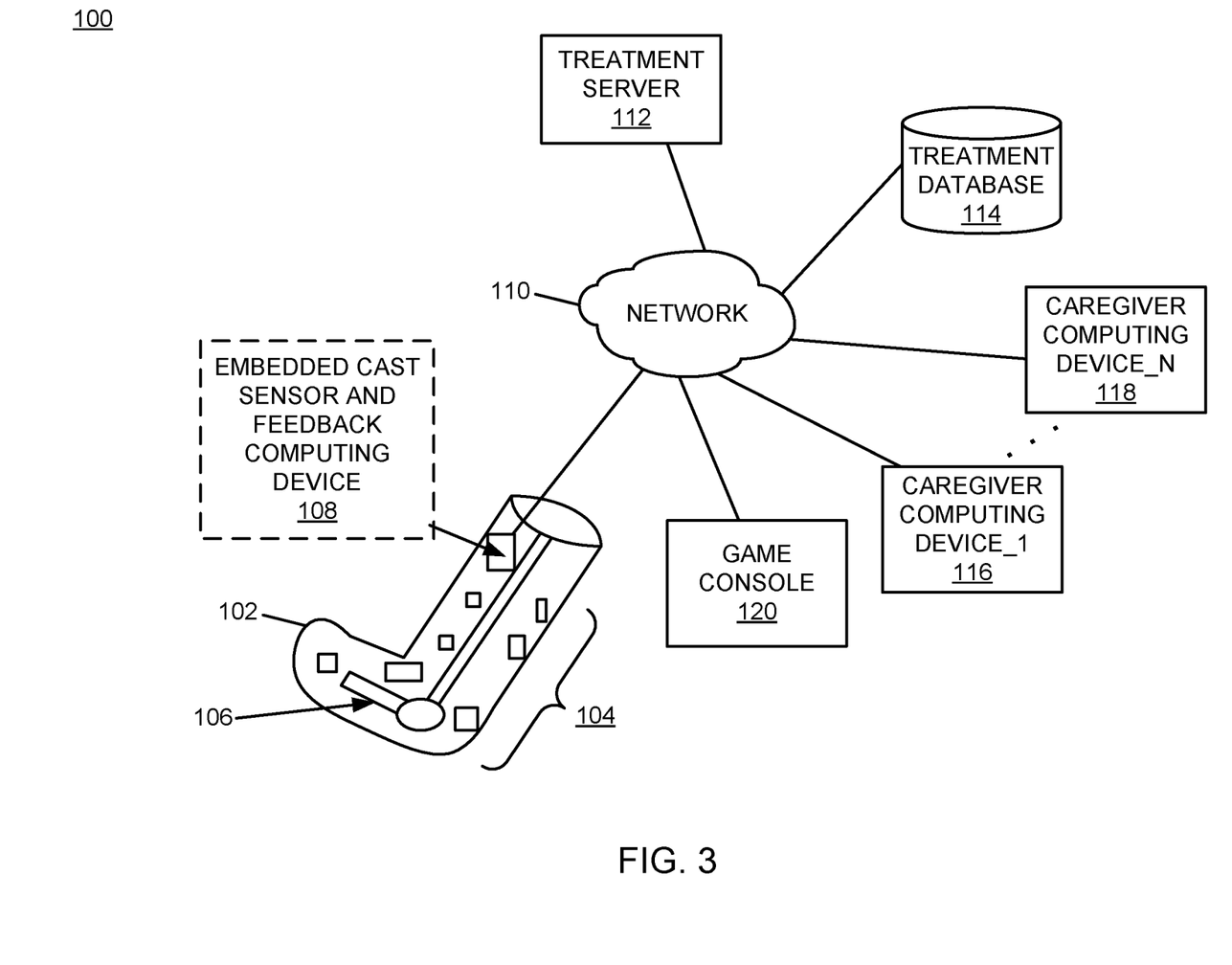
FIG. 3 is a block diagram of an example of an implementation of a system for technological congenital talipes equino varus (CTEV) treatment success rate improvement according to an embodiment of the present subject matter.
Figure 4:
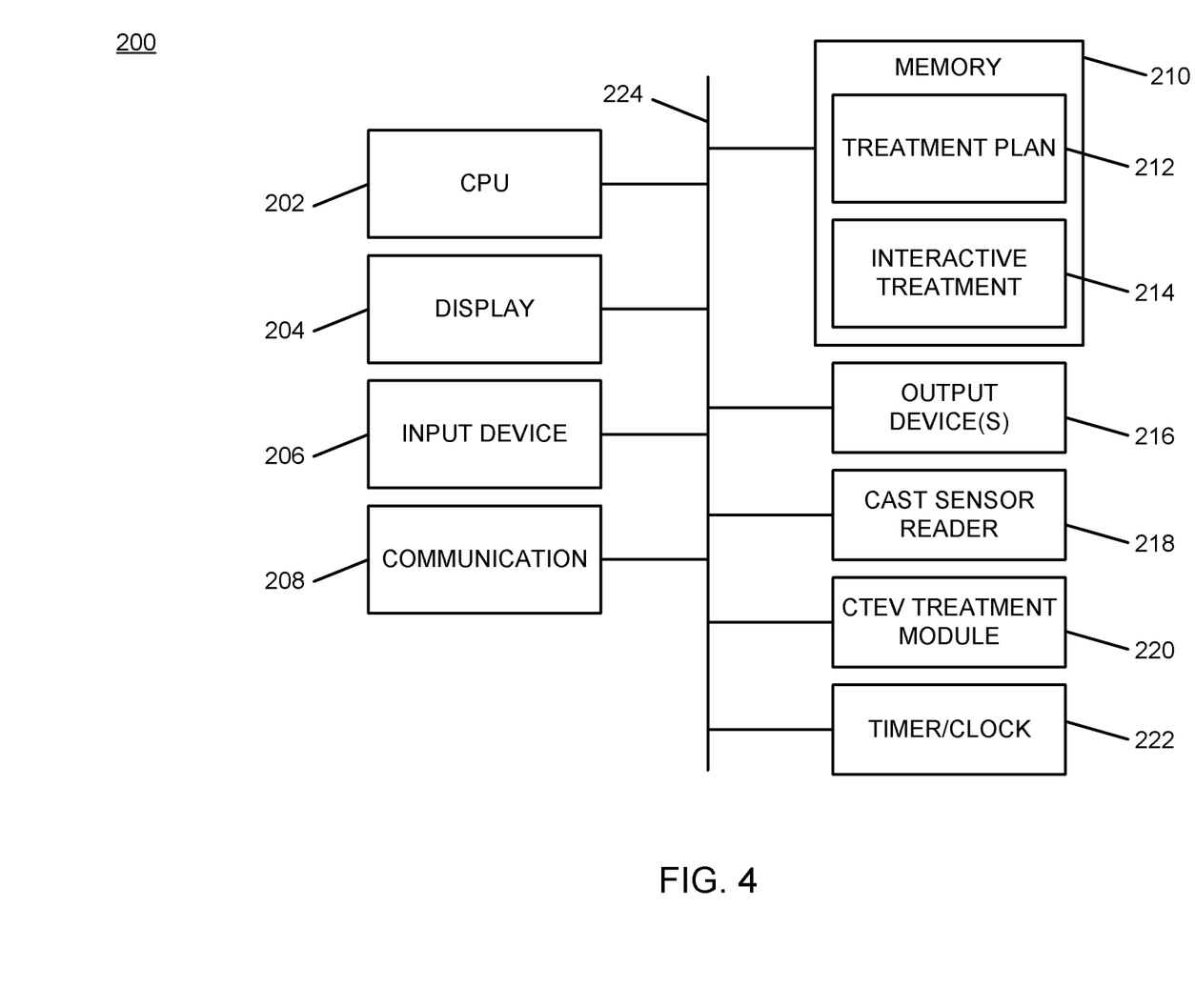
FIG. 4 is a block diagram of an example of an implementation of a core processing module capable of performing technological CTEV treatment success rate improvement according to an embodiment of the present subject matter.

Regarding alternative platform implementation options, FIG. 3 below is directed to such alternatives, while FIG. 4 is directed to module-level implementation options usable within any of the platform implementation options described herein. It should be understood that the various alternatives may be combined with or substituted with the implementation options described above and below, as appropriate for the given implementation.

FIG. 3 is a block diagram of an example of an implementation of a system 100 for technological congenital talipes equino varus (CTEV) treatment success rate improvement. A sensor-based cast 102 is illustrated, and is wearable by a patient. The sensor-based cast 102 represents one possible implementation of an Internet of things (IoT) medical treatment (IoT-MT) device, as described above. The system 100 represents one possible implementation of a medical treatment system, as also described above.

The sensor-based cast 102 includes several (a plurality of) cast sensors 104, a mechanical adjustable positioning system 106 that sets and records wear angles relative to a previous foot angle or a target foot angle, and an embedded cast sensor and feedback computing device 108. The embedded cast sensor and feedback computing device 108 is alternatively termed the "ECSF" device 108 for brevity herein. The sensor-based cast 102 in combination with the several cast sensors 104, the mechanical adjustable positioning system 106, and the ECSF device 108 is understood to represent one example implementation of an IoT-MT device, as described above and elsewhere herein.

The cast sensors 104 are not individually labeled within FIG. 3 due to scale differences and perspective within the drawing and to avoid crowding in the drawing. However, it should be understood that each of the cast sensors 104 may be selectively integrated with the sensor-based cast 102 to achieve a variety of CTEV treatment improvements. As described above, the cast sensors 104 can include a variety of integrated real-time sensors. Specifically, the cast sensors 104 can include one or more contact and/or pressure sensors and an integrated timer/clock to obtain wear time durations and wear time(s) of day during which the patient wears the IoT-MT device, a heartbeat sensor and a thermometer to sense patient heartbeat and temperature, a strain gauge that measures rotational tension around an axis of the foot to record tension on the foot, and an accelerometer and a gyroscope to measure and record activity and position data throughout the treatment. While the sensor types described provide a foundation for the examples described herein, many other types of sensors may be used to implement the features described herein, and all such sensors are considered within the scope of the present description.

Returning to the description of FIG. 3, the ECSF device 108 communicates via a network 110 with several other devices. The other devices include a treatment server 112 within which a patient treatment plan may be created and evaluated over time by a doctor, a treatment database 114 within which to store and distribute a patient treatment plan, a caregiver computing device_1 116 through a caregiver computing device_N 118 that provide one or more caregivers and the patient real-time treatment feedback to promote treatment compliance and success, and a game console 120 to allow the patient and/or a caregiver to interactively play games designed to assist with technological CTEV treatment success rate improvement. It is understood that the caregiver computing device_1 116 through the caregiver computing device_N 118 may be utilized by a doctor (to create a patient treatment plan and to evaluate progress over time), by a patient (to interactively perform activities associated with the patient treatment plan), and by a guardian (to assist and engage with the patient to help with the patient treatment plan). Further, the game console 120 may be integrated with the ECSF device 108, either by wired or wireless communications inclusive of or separate from the network 110. Additionally or alternatively, any of the caregiver computing device_1 116 through the caregiver computing device_N 118 may operate as a game controller or game controller interface (e.g., for a caregiver), as appropriate for the given implementation. It is additionally noted that the ECSF device 108 additionally may be configured to provide feedback in the form of audio or visual cues to alert the patient or a caregiver of suggested adjustments to the mechanical adjustable positioning system 106 and/or the patient's use of the sensor-based cast 102 for technological CTEV treatment success rate improvement.

Additionally, the treatment server 112 and the treatment database 114 can provide an integrated gaming and/or learning system that integrates the ECSF device 108, and thereby integrates with the cast sensors 104, with the remote server-based platform(s) to facilitate gaming and other real-time activities by the patient as well as real-time treatment analysis for the doctor and caregiver(s). As such, the patient and/or caregiver(s) can utilize either the gaming console 120, or the integrated gaming and/or learning system provided by the treatment server 112 and the treatment database 114, to participate in treatment-related games, as appropriate for the given implementation. The patient's participation in the games or other real-time activities may be promoted via output generated for the patient by the ECSF device 108 as audio and/or visual cues/instructions, and video and/or audio output may also be generated on any of the caregiver computing device_1 116 through the caregiver computing device_N 118 for use by the patient and caregiver(s). The patient and/or caregiver(s) can play games together or the patient may individually play games with game inputs provided by the cast sensors 104 and the caregiver computing device_1 116 through the caregiver computing device_N 118. Game outputs can be provided on a combination of the ECSF device 108 and the caregiver computing device_1 116 through the caregiver computing device_N 118, as appropriate for the given implementation.

As will be described in more detail below in association with FIG. 4 through FIG. 6, the ECSF device 108 in functional combination with the treatment server 112, the treatment database 114, and the caregiver computing device_1 116 through the caregiver computing device_N 118 provide an integrated and distributed computing platform for technological CTEV treatment success rate improvement. The technological CTEV treatment success rate improvement described herein provides technological advancements in cast sensing technology in combination with technological integration of cast sensor measurements and feedback with patient treatment plans and caregiver support and supervision. By use of the technology described herein, congenital talipes equino varus (CTEV) may be effectively cured across a multitude of patients, thereby improving CTEV treatment quality in a way that was not previously possible using prior conventional approaches to CTEV treatment.

In view of the implementation alternatives described above, the present technology may be implemented within a cloud computing platform, at a user computing device, at a server device level, or by a combination of such platforms and devices as appropriate for a given implementation. A variety of possibilities exist for implementation of the present subject matter, and all such possibilities are considered within the scope of the present subject matter.

The network 110 may include any form of interconnection suitable for the intended purpose, including a private or public network such as an intranet or the Internet, respectively, direct inter-module interconnection, dial-up, wireless, or any other interconnection mechanism capable of interconnecting the respective devices.

The treatment server 112 may include any device capable of providing data for consumption by a device, such as the ECSF device 108 and the caregiver computing device_1 116 through the caregiver computing device_N 118, via a network, such as the network 110. As such, the treatment server 112 can include a physician's treatment server in the form of a web server, application server, or other data server device.

The treatment database 114 may include a relational database, an object database, or any other storage type of device. As such, the treatment database 114 may be implemented as appropriate for a given implementation.

FIG. 4 is a block diagram of an example of an implementation of a core processing module 200 capable of performing technological CTEV treatment success rate improvement. The core processing module 200 may be associated with any of the devices described within FIG. 3, including the ECSF device 108, the treatment server 112, the treatment database 114, and the caregiver computing device_1 116 through the caregiver computing device_N 118, or with devices within the cloud computing environment 50, as appropriate for a given implementation. As such, the core processing module 200 is described generally herein, though it is understood that many variations on implementation of the components within the core processing module 200 are possible and all such variations are within the scope of the present subject matter. It is understood that for certain implementations, such as the ECSF device 108 of the sensor-based cast 102, the cast sensors 104 may form a portion of the core processing module 200. In other implementations, the cast sensors 104 may be implemented as an IoT service within a cloud computing platform and the core processing module 200 may receive messages from the cast sensors 104 via the IoT service. Further, the core processing module 200 may be implemented as an embedded processing device with circuitry designed specifically to perform the processing described herein as appropriate for a given implementation, such as with the ECSF device 108 and any of the caregiver computing device_1 116 through the caregiver computing device_N 118 described in association with FIG. 3. For example, the caregiver computing device_1 116 through the caregiver computing device_N 118 may be implemented as wearable devices, such as a watch that integrates CTEV treatment input and output for the patient and/or caregiver(s).

Further, the core processing module 200 may provide different and complementary processing of CTEV treatment inputs and outputs in association with each implementation. As such, for any of the examples below, it is understood that any aspect of functionality described with respect to any one device that is described in conjunction with another device (e.g., sends/sending, etc.) is to be understood to concurrently describe the functionality of the other respective device (e.g., receives/receiving, etc.).

A central processing unit (CPU) 202 ("processor" or "application-specific" processor) provides hardware that performs computer instruction execution, computation, and other capabilities within the core processing module 200. A display 204 provides visual information to a user of the core processing module 200 and an input device 206 provides input capabilities for the user.

The display 204 may include any display device, such as a cathode ray tube (CRT), liquid crystal display (LCD), light emitting diode (LED), electronic ink displays, projection, touchscreen, or other display element or panel. The input device 206 may include a computer keyboard, a keypad, a mouse, a pen, a joystick, touchscreen, voice command processing unit, or any other type of input device by which the user may interact with and respond to information on the display 204.

It should be noted that the display 204 and the input device 206 may be optional components for the core processing module 200 for certain implementations/devices, or may be located remotely from the respective devices and hosted by another computing device that is in communication with the respective devices. Accordingly, the core processing module 200 may operate as a completely automated embedded device without direct user configurability or feedback. However, the core processing module 200 may also provide user feedback and configurability via the display 204 and the input device 206, respectively, as appropriate for a given implementation.

A communication module 208 provides hardware, protocol stack processing, and interconnection capabilities that allow the core processing module 200 to communicate with other modules within the system 100, or within the cloud computing environment 50, as appropriate for a given implementation. The communication module 208 may include any electrical, protocol, and protocol conversion capabilities useable to provide interconnection capabilities, as appropriate for a given implementation. As such, the communication module 208 represents a communication device capable of carrying out communications with other devices. The communication module 208 may further include one or more wireless communication capabilities, as appropriate for the given implementation, such as with the ECSF device 108.

A memory 210 includes a treatment plan storage area 212 that stores one or more patient treatment plans, treatment feedback, and other treatment-related information within the core processing module 200. The memory 210 also includes an interactive treatment module 214 that provides computing interaction with the patient and caregiver(s), such as in the form of real-time games, sensor measurements, and audio/visual feedback.

It is understood that the memory 210 may include any combination of volatile and non-volatile memory suitable for the intended purpose, distributed or localized as appropriate, and may include other memory segments not illustrated within the present example for ease of illustration purposes. For example, the memory 210 may include a code storage area, an operating system storage area, a code execution area, and a data area without departure from the scope of the present subject matter.

One or more output device(s) 216 can include light emitting diodes (LEDs), audio outputs (e.g., speakers, chimes, bells, buzzers, etc.), and other output devices as appropriate for a given implementation. A cast sensor reader 218 may receive input from the cast sensors 104, again for either an implementation of the ECSF device 108 of the sensor-based cast 102, or for a cloud based IoT service from which cast sensor readings are received.

A CTEV treatment module 220 is also illustrated. The CTEV treatment module 220 provides customizable real-time treatment control functionality for the core processing module 200, as described above and in more detail below. The CTEV treatment module 220 implements the automated technological CTEV treatment success rate improvement of the core processing module 200.

It should also be noted that the CTEV treatment module 220 may form a portion of other circuitry described without departure from the scope of the present subject matter. The CTEV treatment module 220 may form a portion of an interrupt service routine (ISR), a portion of an operating system, or a portion of an application without departure from the scope of the present subject matter. The CTEV treatment module 220 may also include an embedded device with circuitry designed specifically to perform the processing described herein as appropriate for a given implementation.

A timer/clock module 222 is illustrated and used to determine timing and date information, such as times of wearing and active patient use of the sensor-based cast 102, as described above and in more detail below. As such, the CTEV treatment module 220 may utilize information derived from the timer/clock module 222 for information processing activities, such as the technological CTEV treatment success rate improvement described herein.

While not separately illustrated in FIG. 4, it is understood that the treatment database 114 may be associated with the core processing module 200. As such, the treatment database 114 may be operatively coupled to the core processing module 200 without use of network connectivity, as appropriate for a given implementation.

The CPU 202, the display 204, the input device 206, the communication module 208, the memory 210, the output device(s) 216, the cast sensor reader 218, the CTEV treatment module 220, and the timer/clock 222 are interconnected via an interconnection 224. The interconnection 224 may include a system bus, a network, or any other interconnection capable of providing the respective components with suitable interconnection for the respective purpose.

Though the different modules illustrated within FIG. 4 are illustrated as component-level modules for ease of illustration and description purposes, it should be noted that these modules may include any hardware, programmed processor(s), and memory used to carry out the functions of the respective modules as described above and in more detail below. For example, the modules may include additional controller circuitry in the form of application specific integrated circuits (ASICs), processors, antennas, and/or discrete integrated circuits and components for performing communication and electrical control activities associated with the respective modules. Additionally, the modules may include interrupt-level, stack-level, and application-level modules as appropriate. Furthermore, the modules may include any memory components used for storage, execution, and data processing for performing processing activities associated with the respective modules. The modules may also form a portion of other circuitry described or may be combined without departure from the scope of the present subject matter.

Additionally, while the core processing module 200 is illustrated with and has certain components described, other modules and components may be associated with the core processing module 200 without departure from the scope of the present subject matter. Additionally, it should be noted that, while the core processing module 200 is described as a single device for ease of illustration purposes, the components within the core processing module 200 may be co-located or distributed and interconnected via a network without departure from the scope of the present subject matter. Many other possible arrangements for components of the core processing module 200 are possible and all are considered within the scope of the present subject matter. Accordingly, the core processing module 200 may take many forms and may be associated with many platforms.

Figure 5:
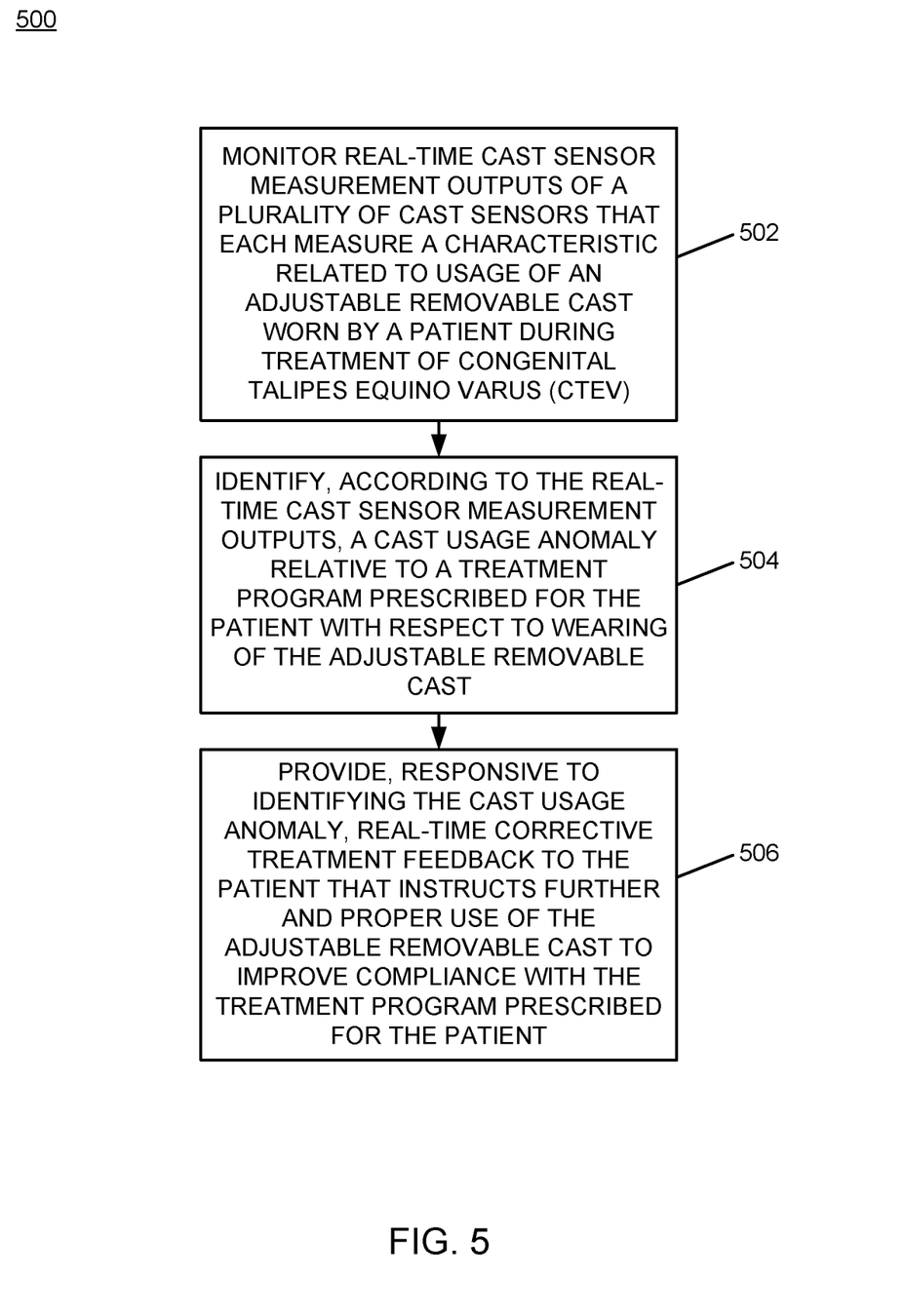
FIG. 5 is a flow chart of an example of an implementation of a process for technological CTEV treatment success rate improvement.
Figure 6:
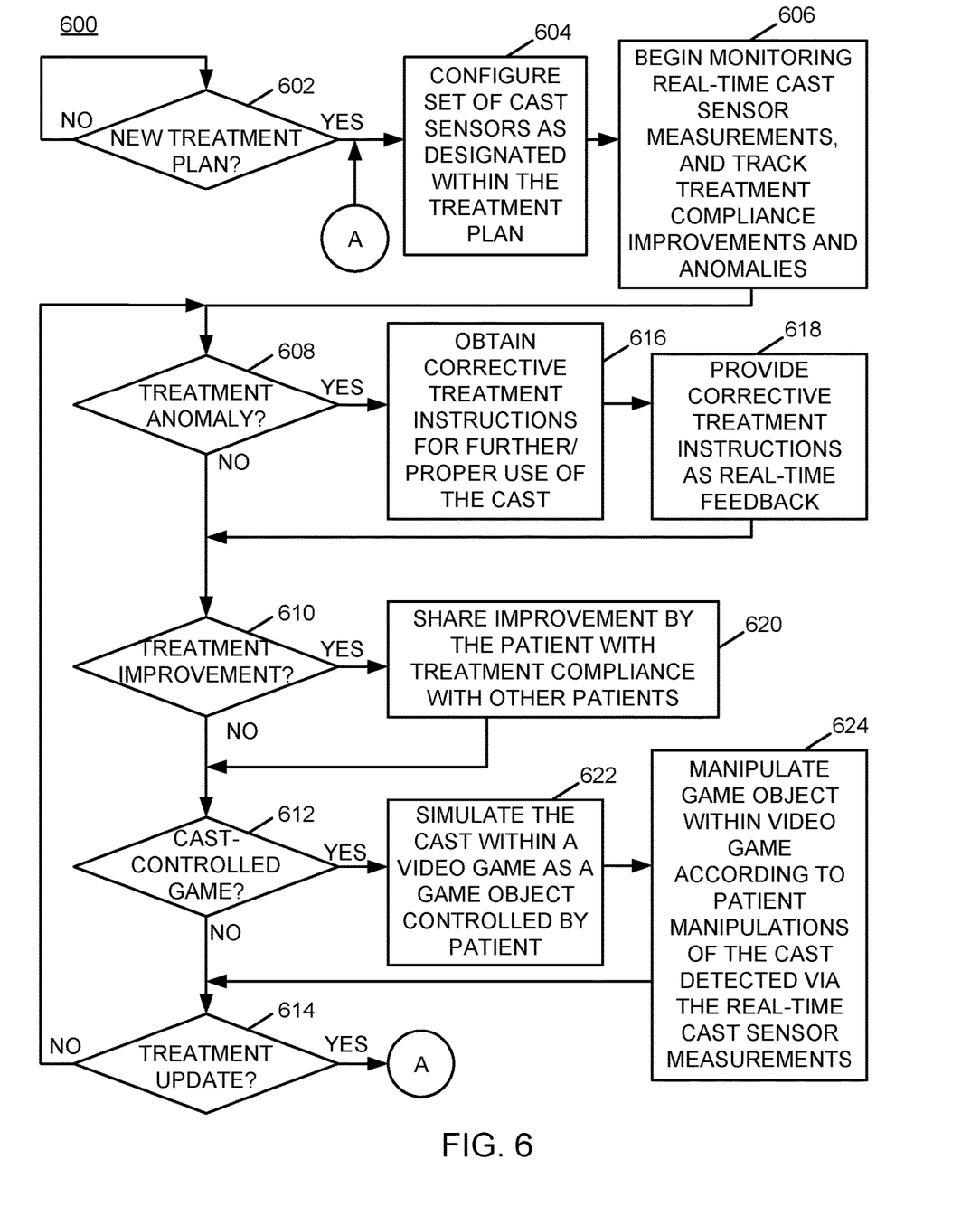
FIG. 6 is a flow chart of an example of an implementation of a process for technological CTEV treatment success rate improvement that integrates peer/patient support and gamification into the CTEV treatment process according to an embodiment of the present subject matter.

FIG. 5 through FIG. 6 described below represent example processes that may be executed by devices, such as the core processing module 200, to perform the automated technological CTEV treatment success rate improvement associated with the present subject matter. Many other variations on the example processes are possible and all are considered within the scope of the present subject matter. The example processes may be performed by modules, such as the CTEV treatment module 220 and/or executed by the CPU 202, associated with such devices. It should be noted that time out procedures and other error control procedures are not illustrated within the example processes described below for ease of illustration purposes. However, it is understood that all such procedures are considered to be within the scope of the present subject matter. Further, the described processes may be combined, sequences of the processing described may be changed, and additional processing may be added or removed without departure from the scope of the present subject matter.

FIG. 5 is a flow chart of an example of an implementation of a process 500 for technological CTEV treatment success rate improvement. The process 500 represents a computer-implemented method of performing the technological integrated cast processing described herein. At block 502, the process 500 monitors real-time cast sensor measurement outputs of a set of cast sensors that each measure a characteristic related to usage of an adjustable removable cast worn by a patient during treatment of congenital talipes equino varus (CTEV). At block 504, the process 500 identifies, according to the real-time cast sensor measurement outputs, a cast usage anomaly relative to a treatment program prescribed for the patient with respect to wearing of the adjustable removable cast. At block 506, the process 500 provides, responsive to identifying the cast usage anomaly, real-time corrective treatment feedback to the patient that instructs further and proper use of the adjustable removable cast to improve compliance with the treatment program prescribed for the patient.

FIG. 6 is a flow chart of an example of an implementation of a process 600 for technological CTEV treatment success rate improvement that integrates peer/patient support and gamification into the CTEV treatment process. The process 600 represents a computer-implemented method of performing the technological integrated cast processing described herein. At decision point 602, the process 600 makes a determination as to whether a new treatment plan/program has been created by a doctor to treat a patient that suffers from congenital talipes equino varus (CTEV). The treatment plan may be detected to have been created within the treatment database 114 by use of an interface to the treatment server 112 used by the doctor, and the treatment plan can be accessed and/or retrieved as appropriate for the given implementation.

In response to determining that a new treatment plan/program has been created by a doctor to treat a patient that suffers from CTEV, the process 600 configures a set of cast sensors as designated within the treatment plan at block 604. As described above, a variety of real-time cast sensors, such as the cast sensors 104, may be selectively used as appropriate for any stage of a treatment plan. Each cast sensor may measure a characteristic related to usage of an adjustable removable cast worn by a patient during treatment of CTEV. At block 606, the process 600 begins monitoring real-time cast sensor measurement outputs from the configured cast sensors, and begins tracking treatment compliance improvements and anomalies relative to the treatment plan. The monitoring of the real-time cast sensor measurement outputs includes monitoring characteristics related to the usage of the adjustable removable cast measured by the set of cast sensors. The real-time cast sensor measurement outputs include one or more of rotational force around an axis of a foot of the patient (e.g., by use of a strain gauge), wear angle settings of the adjustable removable cast (e.g., using the mechanical adjustable positioning system 106), movement of the foot within the adjustable removable cast (e.g., using one or more pressure sensors), force applied by the foot to the adjustable removable cast at a location of a cast sensor (e.g., again using pressure sensors), time of day and length of time the adjustable removable cast is worn by the patient (e.g., using an integrated timer/clock), patient heartbeat and/or temperature (e.g., using a heartbeat sensor and/or a thermometer), and patient activity and position during the treatment program (e.g., using an accelerometer and/or gyroscope). Other real-time cast sensor measurements are possible, and all are considered to be within the scope of the present description.

At decision point 608, the process 600 begins iterative processing to perform a variety of integrated operations by determining whether a treatment anomaly has been detected during the real-time monitoring and tracking using the real-time cast sensor measurements. Higher-level processing will be described herein first, followed by details of the individual processing operations. As such, in response to determining that a treatment anomaly has not been detected, the process 600 makes a determination at decision point 610 as to whether a treatment improvement has been detected. In response to determining that a treatment improvement has not been detected, the process 600 makes a determination at decision point 612 as to whether a cast-controlled game has been requested to be started by a patient or caregiver. In response to determining that a cast-controlled game has not been requested to be started by a patient or caregiver, the process 600 makes a determination at decision point 614 as to whether a treatment update has been specified by the doctor. In response to determining that a treatment update has been specified by the doctor, the process 600 returns to block 604 (as illustrated within the drawing figure using the circled "A") to re-configure the set of cast sensors as designated in the updated treatment plan, and the process iterates as described above to monitor the real-time cast sensor measurements and track treatment improvements and anomalies. As such, the process 600 iteratively adjusts the configuration of the set of cast sensors over time in response to changes of the treatment program prescribed for the patient. Alternatively, in response to determining at decision point 614 that a treatment update has not been specified by the doctor, the process 600 returns to decision point 608 and iterates as described above.

Returning to the description of decision point 608, a treatment anomaly may be detected according to the real-time cast sensor measurement outputs, and a determination can be made that a cast usage anomaly relative to the treatment plan/program prescribed for the patient with respect to wearing of the adjustable removable cast has been identified. In response to determining that a treatment anomaly has been detected during the real-time monitoring and tracking using the real-time cast sensor measurements, the process 600 obtains corrective treatment instructions for further/proper use of the cast at block 616. At block 618, the process 600 provides corrective treatment instructions as real-time corrective treatment feedback to the patient. The real-time corrective treatment feedback instructs the further and proper use of the adjustable removable cast to improve patient compliance with the treatment program prescribed for the patient. The process 600 may, for example, provide a notification of the real-time corrective treatment feedback as an electronic message sent to one of a smartphone, a tablet, and a game console of one of a doctor, a parent, or a guardian of the patient to allow the doctor, the parent, or the guardian to assist the patient with improving compliance with the treatment program prescribed for the patient. The process 600 may additionally and/or alternatively provide a notification of the real-time corrective treatment feedback as an electronic message sent to one of a smartphone, a tablet, and a game console designated to receive real-time corrective feedback notifications by one of a doctor, a parent, or a guardian of the patient to allow one of the doctor, the parent, or the guardian to assist the patient with social reinforcement of compliance with the treatment program prescribed for the patient. The process 600 returns to decision point 610, and iterates as described above.

Returning to the description of decision point 610, in response to determining that a treatment improvement by the patient with the compliance with the treatment program prescribed for the patient has been detected, the process 600 shares the treatment improvement with one or more other patients undergoing a similar treatment program to build a support network for the patient at block 620. The process 600 may additionally and/or alternatively provide an electronic message sent to one of a smartphone, a tablet, and a game console designated to receive real-time treatment improvement notifications by one of a doctor, a parent, or a guardian of the patient to allow one of the doctor, the parent, or the guardian to receive real-time notifications of the patient's compliance with the treatment program prescribed for the patient. The process 600 returns to decision point 612, and iterates as described above.

Returning to the description of decision point 612, in response to determining that a cast-controlled game has been requested to be started by a patient or caregiver, the process 600 simulates the cast within a video game as a game object controlled by the patient using the cast at block 622. Simulation of the cast within the video game includes utilizing the real-time cast sensor measurement outputs as video game inputs to a video game console to allow the patient to play the video game using the adjustable removable cast as a video game controller. Further, simulation of the cast as a game object may include simulating the cast as any game object that may be utilized by a game participant represented within the video game. For example, the adjustable removable cast can be simulated within the video game as a game object worn by the patient within the video game, and controlled within the video game using the monitored real-time cast sensor measurement outputs that result from patient manipulations of the adjustable removable cast. Within such an implementation, the adjustable removable cast can additionally be simulated within the video game as game object in the form of a surfboard, a skateboard, a roller skate, a bike shoe, or other game object, as appropriate for a given implementation. As described above, the patient and/or caregiver(s) can utilize either the gaming console 120, or the integrated gaming and/or learning system provided by the treatment server 112 and the treatment database 114, to participate in treatment-related games, as appropriate for the given implementation.

At block 624, the process 600 manipulates the game object within the video game according to the patient manipulations of the cast detected via the real-time cast sensor measurements. The process 600 continues to allow the patient to manipulate the game object and play the game until the patient indicates a request to stop playing the video game (e.g., by applying pressure to a particular configured pressure sensor). In response to completion of video game play by the patient, the process 600 returns to decision point 614 and iterates as described above.

As such, the process 600 utilizes a variety of different cast sensors to detect real-time sensor output measurements, and utilizes the real-time sensor output measurements to detect anomalies and compliance with a treatment program by a patient. The process 600 additionally provides a gaming interface for the patient that allows the patient to become engaged in the use of the cast for improved treatment success.

Some embodiments of the present invention may improve the technology of computers in at least one, or more, of the following ways: (i) by integration of a variety of sensors into a cast that improves real-time cast usage sensing and treatment augmentation for a patient during a critical treatment time period, (ii) by integrating a technological treatment program across multiple devices, and (iii) by providing a real-time treatment feedback loop that improves implementation of and compliance with treatment changes.

The present invention is not abstract because it relates particularly to computer operations and/or hardware for reasons that may at least include the following: (i) it provides a completely new computing device in the form of a technological patient treatment cast with an embedded controller and embedded sensors usable to monitor and augment a treatment program at a location remote from the attending doctor, (ii) it provides a distributed computing platform that engages a patient and caregivers in a manner that was not previously technologically possible, and (iii) it provides technological treatment processes and integrated equipment/sensors with real-time feedback by use of the integrated patient treatment cast that were not possible using prior/conventional computers and computing technology.

As described above in association with FIG. 1 through FIG. 6, the example systems and processes provide technological CTEV treatment success rate improvement. Many other variations and additional activities associated with technological CTEV treatment success rate improvement are possible and all are considered within the scope of the present subject matter.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art based upon the teachings herein without departing from the scope and spirit of the invention. The subject matter was described to explain the principles of the invention and the practical application, and to enable others of ordinary skill in the art to understand the invention for various embodiments with various modifications as are suited to the particular use contemplated.

What is claimed is:

1. A computer-implemented method of computer-controlled therapy, comprising:
   by a processor device:
      monitoring real-time cast sensor measurement outputs of a plurality of cast sensors that each measure a characteristic related to usage of an adjustable removable cast worn by a patient during treatment of congenital talipes equino varus (CTEV);
      identifying, according to the real-time cast sensor measurement outputs, a cast usage anomaly relative to a treatment program prescribed for the patient with respect to wearing of the adjustable removable cast; and
      providing, responsive to identifying the cast usage anomaly, real-time corrective treatment feedback to the patient that instructs further and proper use of the adjustable removable cast to improve compliance with the treatment program prescribed for the patient.

2. The computer-implemented method of computer-controlled therapy of claim 1, further comprising the processor:
   utilizing the real-time cast sensor measurement outputs as video game inputs to a video game console to allow the patient to play a video game using the adjustable removable cast as a video game controller; and
   simulating the adjustable removable cast within the video game as a game object worn by the patient within the video game and controlled within the video game using the monitored real-time cast sensor measurement outputs that result from patient manipulations of the adjustable removable cast, where the game object is selected from a group consisting of a surfboard, a skateboard, a roller skate, and a bike shoe.

3. The computer-implemented method of computer-controlled therapy of claim 1, further comprising the processor tracking improvement by the patient with the compliance with the treatment program prescribed for the patient.

4. The computer-implemented method of computer-controlled therapy of claim 1, further comprising the processor sharing improvement by the patient with the compliance with the treatment program prescribed for the patient with other patients undergoing a similar treatment program to build a support network for the patient.

5. The computer-implemented method of computer-controlled therapy of claim 1, further comprising the processor providing a notification of the real-time corrective treatment feedback as an electronic message sent to one of a smartphone, a tablet, and a game console of one of a doctor, a parent, or a guardian of the patient to allow the doctor, the parent, or the guardian to assist the patient with improving the compliance with the treatment program prescribed for the patient.

6. The computer-implemented method of computer-controlled therapy of claim 1, further comprising the processor:
   configuring the plurality of cast sensors as designated within the treatment program prescribed for the patient; and
   iteratively adjusting the configuration of the plurality of cast sensors over time in response to changes of the treatment program prescribed for the patient.

7. The computer-implemented method of computer-controlled therapy of claim 1, where software is provided as a service in a cloud environment, and where the characteristics related to the usage of the adjustable removable cast and measured by the plurality of cast sensors are selected from a group consisting of:
   (i) rotational force around an axis of a foot of the patient;
   (ii) wear angle settings of the adjustable removable cast;
   (iii) movement of the foot within the adjustable removable cast;
   (iv) force applied by the foot to the adjustable removable cast at a location of a cast sensor;
   (v) time of day and length of time the adjustable removable cast is worn by the patient;
   (vi) patient heartbeat or temperature; and
   (vii) patient activity and position during the treatment program.

8. A system, comprising:
   a plurality of cast sensors integrated into a cast; and
   a processor programmed to:
      monitor real-time cast sensor measurement outputs of the plurality of cast sensors that each measure a characteristic related to usage of an adjustable removable cast worn by a patient during treatment of congenital talipes equino varus (CTEV);
      identify, according to the real-time cast sensor measurement outputs, a cast usage anomaly relative to a treatment program prescribed for the patient with respect to wearing of the adjustable removable cast; and
      provide, responsive to identifying the cast usage anomaly, real-time corrective treatment feedback to the patient that instructs further and proper use of the adjustable removable cast to improve compliance with the treatment program prescribed for the patient.

9. The system of claim 8, where the processor is further programmed to:
   utilize the real-time cast sensor measurement outputs as video game inputs to a video game console to allow the patient to play a video game using the adjustable removable cast as a video game controller; and
   simulate the adjustable removable cast within the video game as a game object worn by the patient within the video game and controlled within the video game using the monitored real-time cast sensor measurement outputs that result from patient manipulations of the adjustable removable cast, where the game object is selected from a group consisting of a surfboard, a skateboard, a roller skate, and a bike shoe.

10. The system of claim 8, where the processor is further programmed to one of:
track improvement by the patient with the compliance with the treatment program prescribed for the patient; and
share the improvement by the patient with the compliance with the treatment program prescribed for the patient with other patients undergoing a similar treatment program to build a support network for the patient.

11. The system of claim 8, where the processor is further programmed to:
provide a notification of the real-time corrective treatment feedback as an electronic message sent to one of a smartphone, a tablet, and a game console of one of a doctor, a parent, or a guardian of the patient to allow the doctor, the parent, or the guardian to assist the patient with improving the compliance with the treatment program prescribed for the patient.

12. The system of claim 8, where the processor is further programmed to:
configure the plurality of cast sensors as designated within the treatment program prescribed for the patient; and
iteratively adjust the configuration of the plurality of cast sensors over time in response to changes of the treatment program prescribed for the patient.

13. The system of claim 8, where software is provided as a service in a cloud environment, and where the characteristics related to the usage of the adjustable removable cast and measured by the plurality of cast sensors are selected from a group consisting of:
(i) rotational force around an axis of a foot of the patient;
(ii) wear angle settings of the adjustable removable cast;
(iii) movement of the foot within the adjustable removable cast;
(iv) force applied by the foot to the adjustable removable cast at a location of a cast sensor;
(v) time of day and length of time the adjustable removable cast is worn by the patient;
(vi) patient heartbeat or temperature; and
(vii) patient activity and position during the treatment program.

14. A computer program product, comprising:
a computer readable storage medium having computer readable program code embodied therewith, where the computer readable storage medium is not a transitory signal per se and where the computer readable program code when executed on a computer causes the computer to:
monitor real-time cast sensor measurement outputs of a plurality of cast sensors that each measure a characteristic related to usage of an adjustable removable cast worn by a patient during treatment of congenital talipes equino varus (CTEV);
identify, according to the real-time cast sensor measurement outputs, a cast usage anomaly relative to a treatment program prescribed for the patient with respect to wearing of the adjustable removable cast; and
provide, responsive to identifying the cast usage anomaly, real-time corrective treatment feedback to the patient that instructs further and proper use of the adjustable removable cast to improve compliance with the treatment program prescribed for the patient.

15. The computer program product of claim 14, where the computer readable program code when executed on the computer further causes the computer to:
utilize the real-time cast sensor measurement outputs as video game inputs to a video game console to allow the patient to play a video game using the adjustable removable cast as a video game controller; and
simulate the adjustable removable cast within the video game as a game object worn by the patient within the video game and controlled within the video game using the monitored real-time cast sensor measurement outputs that result from patient manipulations of the adjustable removable cast, where the game object is selected from a group consisting of a surfboard, a skateboard, a roller skate, and a bike shoe.

16. The computer program product of claim 14, where the computer readable program code when executed on the computer further causes the computer to track improvement by the patient with the compliance with the treatment program prescribed for the patient.

17. The computer program product of claim 14, where the computer readable program code when executed on the computer further causes the computer to share improvement by the patient with the compliance with the treatment program prescribed for the patient with other patients undergoing a similar treatment program to build a support network for the patient.

18. The computer program product of claim 14, where the computer readable program code when executed on the computer further causes the computer to provide a notification of the real-time corrective treatment feedback as an electronic message sent to one of a smartphone, a tablet, and a game console of one of a doctor, a parent, or a guardian of the patient to allow the doctor, the parent, or the guardian to assist the patient with improving the compliance with the treatment program prescribed for the patient.

19. The computer program product of claim 14, where the computer readable program code when executed on the computer further causes the computer to:
configure the plurality of cast sensors as designated within the treatment program prescribed for the patient; and
iteratively adjust the configuration of the plurality of cast sensors over time in response to changes of the treatment program prescribed for the patient.

20. The computer program product of claim 14, where software is provided as a service in a cloud environment, and where the characteristics related to the usage of the adjustable removable cast and measured by the plurality of cast sensors are selected from a group consisting of:
(i) rotational force around an axis of a foot of the patient;
(ii) wear angle settings of the adjustable removable cast;
(iii) movement of the foot within the adjustable removable cast;
(iv) force applied by the foot to the adjustable removable cast at a location of a cast sensor;
(v) time of day and length of time the adjustable removable cast is worn by the patient;
(vi) patient heartbeat or temperature; and
(vii) patient activity and position during the treatment program.

* * * * *